US012667316B2

(12) United States Patent　　　(10) Patent No.:　US 12,667,316 B2
　　Sreenivasan et al.　　　　　　　(45) Date of Patent:　　Jun. 30, 2026

(54) PROVIDING SCAN PROGRESS INDICATIONS DURING MEDICAL IMAGING

(71) Applicant: KONINKLIJKE PHILIPS N.V., Eindhoven (NL)

(72) Inventors: Rithesh Sreenivasan, Bengaluru (IN); Krishnamoorthy Palanisamy, Bangalore (IN); Sudipta Chaudhury, Balgalore (IN); Jaap Knoester, Utrecht (NL); Gereon Vogtmeier, Aachen (DE); Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 458 days.

(21) Appl. No.: 18/032,216

(22) PCT Filed: Oct. 20, 2021

(86) PCT No.: PCT/EP2021/079040
§ 371 (c)(1),
(2) Date: Apr. 17, 2023

(87) PCT Pub. No.: WO2022/090013
PCT Pub. Date: May 5, 2022

(65) Prior Publication Data
US 2024/0023901 A1　　　Jan. 25, 2024

(30) Foreign Application Priority Data
Oct. 29, 2020　(EP) ..................................... 20204546

(51) Int. Cl.
*G16H 30/20*　　　(2018.01)
*A61B 5/00*　　　(2006.01)
*A61B 5/055*　　　(2006.01)

(52) U.S. Cl.
CPC ............. *A61B 5/742* (2013.01); *G16H 30/20* (2018.01); *A61B 5/055* (2013.01)

(58) Field of Classification Search
CPC ......... A61B 5/742; A61B 5/055; A61B 6/032; A61B 6/0407; A61B 6/5264;
(Continued)

(56) References Cited

U.S. PATENT DOCUMENTS

2013/0218004 A1*　8/2013　Yang ..................... A61B 5/0033
　　　　　　　　　　　　　　　　　　600/415
2013/0345543 A1　12/2013　Steibel et al.
(Continued)

FOREIGN PATENT DOCUMENTS

EP　　　　3666334 A1　　6/2020
WO　　　2009147608 A1　　12/2009
(Continued)

OTHER PUBLICATIONS

International Search Report and Written Opinion From PCT/EP2021/079040 Mailed Jan. 10, 2022.
(Continued)

*Primary Examiner* — Michael J Brown

(57)　　　　　　ABSTRACT

There is a need for techniques to avoid or reduce motion artifacts in medical images. According to the invention, there is provided control circuitry for a medical imaging system. The control circuitry is configured to control the medical imaging system to provide synchronized display and nudging to provide a patient with information on the progress of a scan. In this way, patient anxiety may be reduced by providing the patient with a sense of time during the scan, leading to a reduction in motion artifacts.

15 Claims, 4 Drawing Sheets

(58) Field of Classification Search
CPC ..... A61B 5/0033; A61B 5/704; A61B 5/7296;
A61B 5/7455; A61B 5/486; G16H 30/20;
A61N 5/0618; A61N 5/1049
USPC .......................................................... 700/56
See application file for complete search history.

(56) References Cited

U.S. PATENT DOCUMENTS

| | | | |
|---|---|---|---|
| 2015/0196780 A1 | 7/2015 | Tijs et al. | |
| 2015/0352375 A1 | 12/2015 | Chen | |
| 2019/0099144 A1 | 4/2019 | Rieger et al. | |
| 2020/0205748 A1 | 7/2020 | Pautsch et al. | |
| 2022/0015722 A1* | 1/2022 | Chaudhury ............ | G16H 40/63 |

FOREIGN PATENT DOCUMENTS

| | | | |
|---|---|---|---|
| WO | 2015044128 A1 | 4/2015 | |
| WO | 2020120529 A1 | 6/2020 | |

OTHER PUBLICATIONS

Long et al "Rendering Volumetric Hapatic Shapes in Mid-Air Using Ultrasound" ACM Transactions on Graphics, vol. 33, No. 6, Nov. 19, 2014 p. 1-10.

* cited by examiner

300

302

300

PROVIDING SCAN PROGRESS INDICATIONS DURING MEDICAL IMAGING

CROSS REFERENCE TO RELATED APPLICATIONS

This application is a U.S. national phase application of International Application No. PCT/EP2021/079040 filed on Oct. 20, 2021, which claims the benefit of EP Application Serial No. 20204546.4 filed Oct. 29, 2020 and is incorporated herein by reference.

FIELD OF THE INVENTION

The invention relates to systems and methods for providing scan progress indications during medical imaging.

BACKGROUND OF THE INVENTION

During an MRI/CT procedure the patient is isolated in the modality room and provided with instructions, for example to remain still, or to hold the breath at particular intervals. The patient is a given a rough idea of the time needed for the scan. For instance, for an MRI/CT spine screening scan, the scan is performed starting from the neck and moves all the way to the lower back. The patient is asked to remain still during the course of the scan, which can take up to 45 minutes. Movement of the patient may lead to motion artifacts in the captured images.

SUMMARY OF THE INVENTION

There is therefore a need for techniques to avoid or reduce motion artifacts in MRI/CT images. This need is met by the subject-matter of the independent claims. Optional features are set forth by the dependent claims.

According to a first aspect, there is provided control circuitry for a medical imaging system. The control circuitry is configured to control the medical imaging system to provide synchronized display and nudging to provide a patient with information on the progress of a scan.

In this way, patient anxiety may be reduced by providing the patient with a sense of time during the scan, leading to a reduction in motion artifacts. This is based on the recognition that, if the patient is informed e.g. at every stage of scan progress, this can reduce patient anxiety and discomfort and thus enable the patient to remain still during the scan. This can also lead to an improved workflow with shorter scans. The claimed subject-matter is particularly advantageous in the context of autonomous imaging where there is no technician providing information and nudging the patient.

In particular, the synchronized display and nudging facilitate the drawing of the patient's attention to a region which is being scanned or which is to be scanned next and which should therefore remain still.

Feedback to the patient concerning progress of the scan may be accompanied by information or instructions concerning periods in which movement is allowed and/or when movement should be minimized to obtain better image quality. An improved workflow may thus be obtained with better patient cooperation.

Aspects of the present disclosure describe personalized and dynamic visual guidance for the patient during the scan, enabled by a smart combination of protocol awareness and patient body detection.

In one advantageous example, the control circuitry is configured to control the medical imaging system to project a scan progress indicator onto the patient's body, in particular onto an anatomical region of the patient's body identified as being relevant for the current or next scan. In this way, the patient's attention is more effectively drawn to the anatomical region such that the anatomical region may be held still to result in better image quality.

The control circuitry may be configured to control the medical imaging system to synchronize modulations in the nudging with changes made to a displayed scan progress indicator. In particular, the control circuitry may be configured to control the medical imaging system to modulate the nudging in synchronization with corresponding modulations made to the display, the synchronized modulations defining a coded signal to be conveyed to the patient. For example, the coded signal may indicate the start or end of the scan or that the scan will start or end after a predetermined time period elapses. The synchronized modulations may have the same frequency and phase. In one particular example, the control circuitry is configured to control the medical imaging system to provide intermittent nudging to an anatomical region of the patient's body in synchronization with flashing of a scan progress indicator projected onto the said anatomical region, to indicate that the said anatomical region is the next to be scanned. In any of these ways, efficient techniques are provided for communicating necessary instructions to the patient as part of a guided human-machine interaction, without requiring disruptive movement from the patient. Patient anxiety may thus be further reduced with consequential enhancements to image quality.

For ready implementability, the control circuitry may further comprise a scan stage identification module configured to identify a stage of the scan based on a predetermined scan sequence; a relevant anatomy identification module configured to identify one or more relevant anatomical regions for the scan; a projection module configured to generate images for display to the patient by a display system of the medical imaging system; a nudging module configured to generate control signals for a nudging system of the medical imaging system; and a synchronization module configured to receive input from the scan stage identification module and from the relevant anatomy identification module and to provide synchronization signals to the projection module and to the nudging module to synchronize the display and nudging.

According to a second aspect, there is provided a medical imaging system comprising the control circuitry of the first aspect.

The medical imaging system may further comprise a display system configured to display images to the patient and a nudging system configured to provide nudging to the patient. The nudging system may comprise a bi-directional nudging and feedback system, where the patient is provided with the information on the progress of the scan as part of a guided human-machine interaction process.

According to a third aspect, there is provided a method for controlling a medical imaging system, the method comprising controlling the medical imaging system to provide synchronized display and nudging to provide a patient with information on the progress of a scan.

The method may comprise controlling the medical imaging system to project a scan progress indicator onto the patient's body, in particular onto an anatomical region of the patient's body identified as being relevant for the current or next scan.

The method may comprise controlling the medical imaging system to synchronize modulations in the nudging with changes made to a displayed scan progress indicator. In particular, the method may comprise controlling the medical imaging system to modulate the nudging in synchronization with corresponding modulations made to the display, the synchronized modulations defining a coded signal to be conveyed to the patient. In one particular example, the method may comprise controlling the medical imaging system to provide intermittent nudging to an anatomical region of the patient's body in synchronization with flashing of a scan progress indicator projected onto the said anatomical region, to indicate that the said anatomical region is the next to be scanned.

The method may further comprise, by a scan stage identification module, identifying a stage of the scan based on a predetermined scan sequence; by a relevant anatomy identification module, identifying one or more relevant anatomical regions for the scan; by a projection module, generating images for display to the patient by a display system of the medical imaging system; by a nudging module, generating control signals for a nudging system of the medical imaging system; and, by a synchronization module, receiving input from the scan stage identification module and from the relevant anatomy identification module and providing synchronization signals to the projection module and to the nudging module to synchronize the display and nudging.

According to a fourth aspect, there is provided a computer program product comprising computer executable instructions which, when executed by a computer, enable the computer to perform the method of the third aspect.

According to a fifth aspect, there is provided a computer readable medium having stored thereon computer executable instructions which, when executed by a computer, enable the computer to perform the method of the third aspect.

According to the first aspect, there may also be provided control circuitry for a medical imaging system, the control circuitry being configured to control the medical imaging system to communicate to a patient multimodal feedback on scan progress. A further aspect proposes a system and method to provide a projected display and synchronized nudging to provide a patient with information on scan progress.

These and other aspects of the invention will be apparent from and elucidated with reference to the embodiments described hereinafter.

The invention may include one or more aspects, examples or features in isolation or combination whether or not specifically disclosed in that combination or in isolation.

BRIEF DESCRIPTION OF THE DRAWINGS

A detailed description will now be given, by way of example only, with reference to the accompanying drawings, in which.

DETAILED DESCRIPTION

Figure 1:
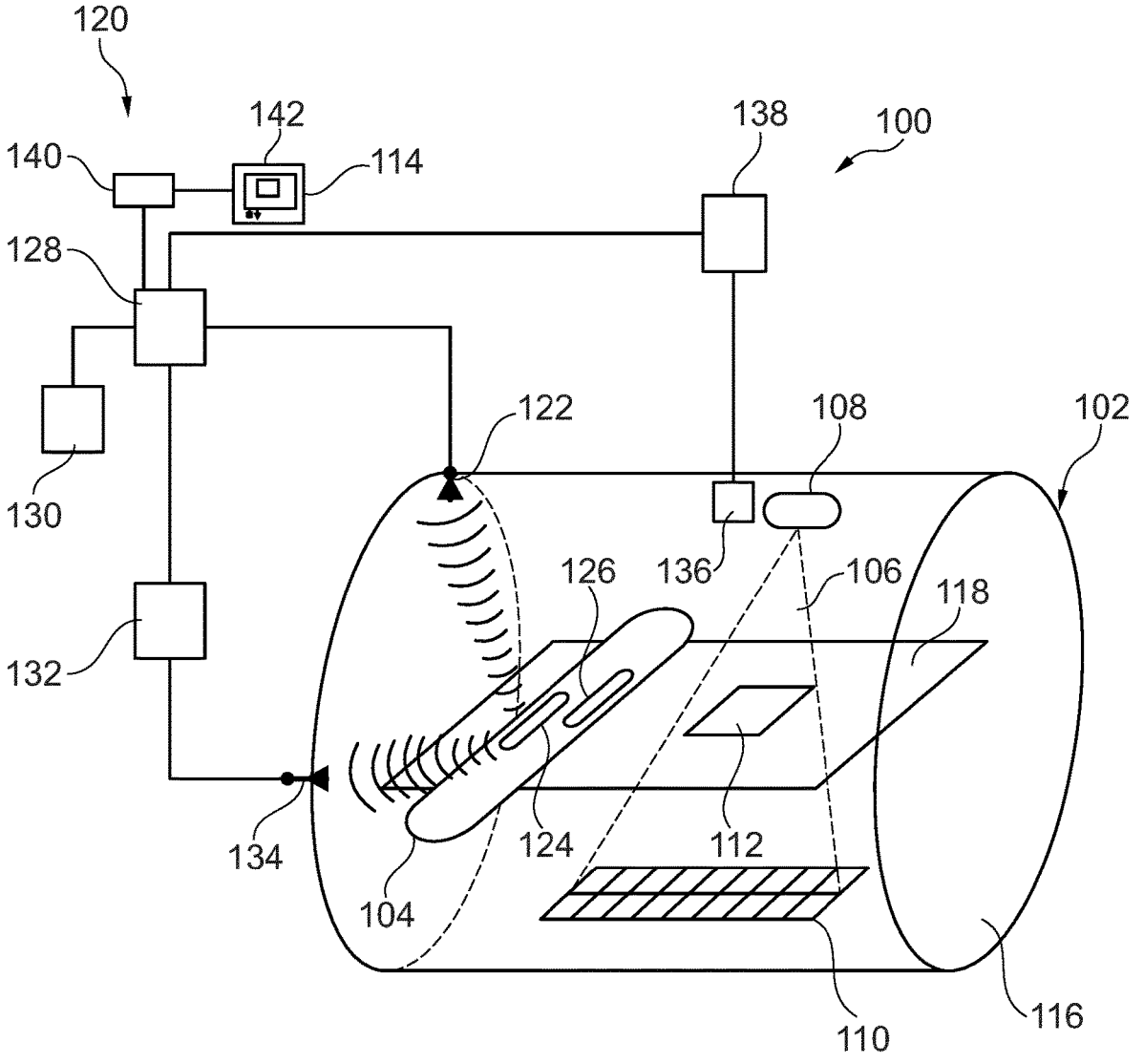
FIG. 1 shows a medical imaging system.

With reference to the schematic block diagram in FIG. 1, there is shown a medical imaging system 100 including an imaging apparatus 102 configured to acquire medical imagery of internal structures of the patient. The imaging apparatus 102 in this example comprises a computed tomography (CT) imaging apparatus ("CT scanner") in which the interrogating imaging signal is an x-ray beam 106 emitted by an x-ray source 108 such as an x-ray tube. The x-ray beam 106 passes through the patient 104, is then modified, in particular attenuated, and the so modified beam is then detected at an x-ray sensitive detector 110. The x-ray sensitive detector 110 is arranged opposite the x-ray source 108 to form therebetween an imaging region 112 where the patient 104 should reside during the imaging. The term "imaging" as used herein is the period throughput which the interrogating imaging signal, such as the x-ray beam 106, passes through the patient 104 and is detected at the detector 110. Intensity data registered at the detector 110 can then be processed by a digital image processor 140 into internal anatomical or functional images 142 rendered for display by a display device 114. The imaging apparatus 102 includes a physical enclosure 116, hereinafter referred to as a bore 116, that surrounds the patient 104 during imaging. The patient 104 resides within the bore 116 during imaging, lying on a support such as an examination table 118 inside the bore 116. The medical imaging system 100 includes a display system 138 including a display screen 136 or optical projection system 136 mounted inside the bore 116, or outside of the bore 116, but in either case so as to display images to the patient whilst the patent is in the bore 116. A user interface 130 provides for further input/output. The medical imaging system 100 also comprises a nudging system 120 for providing nudging to the patient 104, as will now be described. The medical imaging system 100 also comprises control circuitry 128 for controlling operations of the medical image system 100, as will be described further below.

So that the imaging procedure is made more efficient and to maximize information captured in the imagery, it may be important that the specific organ of interest, also referred to herein as the region of interest ("ROI") 126, is positioned in the imaging region 112 during the imaging. The imaging region 112 is a portion of either 2D or 3D space. In order to better support patient positioning, the nudging system 120 (which may also be referred to as a patient positioning system) is provided including one or more transmitters 122 mounted at or inside the bore 116 which can be energized to emit a signal towards the patient 104. The signal emitted by the transmitter 122 causes, from a distance, without physical contact with the patient 104, a haptic sensation on the patient's skin at a certain impact region 124. Examples for causing such haptic sensations include in particular ultrasound transmitters. The one or more transmitters 122 are configured to cause a directed or focused ultrasound beam which can be directed to the desired impact region 124 on the patient 104. The direction of the ultrasound beam is automatically or manually adjustable to impact the desired impact region 124 as will be explained more fully below. The frequency and/or intensity of the ultrasound waves emitted by the transmitter 122 are such that they are capable of simulating mechanoreceptors situated in the patient's skin. The action of the signal emitted by the transmitter 122 is such that it encourages the patient to move to the desired position so that the region of interest 126 is, or remains, within the imaging region 112. Essentially, the transmitter 122 can be used to nudge or usher the patient 104, through the emitted signal, so that patient 104 assumes the correct position and that the region of interest 126 is within the imaging region 112. In the following, the described signal emitted by the one or more transmitters 122 may be referred to herein as the "nudging signal". The emission of such signals to the patient 104 for these purposes is described herein as "nudging". The nudging system 120 includes control circuitry 128 that controls any one or more of various properties of the nudging signal including for example its intensity, frequency, modulation, and direction. The control circuitry 128 controls the transmitter 122 automatically, in particular autonomously, based on a location signal in relation to the patient 104 and/or the ROI 126. In particular, the control circuitry 128 is configured to change properties of the nudging signal based on a distance between the current position of the ROI 126 and the imaging region 112. Changing the nudging signal in this manner includes any one or more of changing the pulse frequency of the nudging signal, changing the intensity of the nudging signal, and changing the frequency of the nudging signal (i.e. of the underlying ultrasound signal). Such fully automatic implementations envisaged herein for autonomous imaging require no or only low level of user action during or in between imaging. In this example, the nudging system 120 takes the form of a bi-directional nudging and feedback system, where the patient is provided with the information on the progress of the scan as part of a guided human-machine interaction process. Since the ultrasound haptic nudging system is inherently a feedback based system, in that it measures the reflected signal, it can in turn compute the displacement (at the targeted region e.g. arms) the patient has made (either intended or unintended), such that any specific movement can be interpreted as feedback from the patient in accordance with a pre scan patient training protocol.

To allow the direction of the nudging signal to be controlled, one or more of the transmitters 122 may be moveable in different spatial orientations. The transmitters 122 may be mounted using a joint, articulated arm, a track or other arrangements that allow movement, including translation and/or rotary movement. A single transmitter 122 may be sufficient if arranged at a suitable vantage location and/or if allowed sufficient motional degrees of freedom. The movement of the transmitter 122 is effected by the control circuitry 128. Specifically, the control circuitry 128 instructs suitable actuators to adjust an orientation of the transmitter 122, and hence the direction of the nudging signal emitted by the transmitters 122. Suitable actuators may include any one or more of servo or stepper motors including mechanical gearing, hydraulics, piezoelectric-element(s), any combination of the foregoing, and/or others.

The transmitter 122 may be arranged as a one- or two-dimensional phased array of ultrasound transducers. The ultrasound transducers are controlled by the control circuitry 128 in a manner so as to create an acoustic interference pattern that gives rise to the directed ultrasound beam that is capable of inducing the haptic sensation on the patient's skin at the impact region 124. The focused ultrasound waves cause, at a distance and in a non-invasive manner, sound sensations at any desired intensity and/or frequency. In embodiments, the acoustic field created by the phased array allows forming volumetric acoustic fields or "haptic shapes", such as a palpable sphere or other geometrical configurations. When applied to the patient 104 at the impact region 124, the patient 104 experiences a sensation as if a physical object of the specified shape is in skin contact. Suitable acoustic shapes such as the mentioned spheres may be used to create a pleasant massage effect for instance, to gently nudge the patient towards the imaging region 112. The nudging signal may be pulsed. The frequency of the pulses and/or intensity of the nudging signal may be held constant throughout the nudging but may also vary. In more detail, the intensity of the nudging signal may drop, the closer the region of interest 126 becomes to the imaging region 112. Proximity information may in addition or instead be modulated by varying a frequency of the pulsation of the nudging signal. The pulse frequency may drop as the ROI 126 moves closer to the imaging region 112. In a similar manner, the frequency of the ultrasound signal itself may be changed. Once the ROI 126 is in the imaging region 112 (that is, once the patient 104 has assumed the correct position), no more nudging signals may be issued by the transmitter 122. If the patient 104 moves (that is, once there is motion of the ROI 126 within the imaging region 112), the transmitter 122 may be re-activated to encourage the patient to assume a posture so that the ROI 126 remains within the imaging region 112. If a portion of the ROI 126 extends outside the imaging region 112, the direction and/or intensity and/or pulse frequency of the nudging signal may be changed accordingly, in dependence on the distance between a current position of the ROI 126 and the position of the imaging region 112.

To provide the above-mentioned location signal, the nudging system 120 includes a locator module 132 that is configured to establish, based on the location signal, the current position of the patient 104, in particular the current position of the ROI 126. The location signal may be received through one or more position sensors 134. The current position of the ROI 126 may be defined relative to a world coordinate system. The world coordinate system may also be used to establish the position of the detector 110 and/or the x-ray source 108. The imaging region 112 may be defined as a patient envelope. This is a portion of space, suitably de-marked by virtual or real demarcations. The locator module 132 is suitably configured to be aware of the spatial extent of the patient envelope. If one part of the ROI 126 extends outside the envelope of the imaging region 112, this is targeted by the transmitter 112 at a suitably chosen impact region 124 to urge the patient 10 to move the extending body part so as to retract within the patient envelope. The position sensors 134 are suitably positioned to receive the incoming location signal from the patient 104 and this incoming location signal is then processed by the locator module 132 to establish the current position of the patient 104, in particular of the ROI 126.

The position sensors 134 may include an optical camera or video-based system. The incoming location signal as received by the position sensors 134 is automatically processed by the locator module 132 into current ROI position information. The position sensors 134 may include a light sensitive sensor (e.g. that of the camera) configured to receive back scattered light caused by surrounding light scattered off the patient 104. The position sensors 134 may include a camera system with a depth sensing or heat sensing (IF) sensor used in addition to or instead of the described optical sensor cameras. The imagery obtained by the position sensors 134 is suitably registered by the locator module 132 to the world coordinate system. An image recognition component in the locator module 132 may be used to analyze the captured imagery to identify in the imagery the patient 104 and, in particular, the ROI 126. The ROI 126 may be defined geometrically by a geometric shape that surrounds the ROI 126. Once the ROI 126 or another anatomical region having a known distance to the ROI 126 has been identified by the locator module 132 in the imagery obtained from the receiver 134, the in-image location is mapped to the world-coordinate system. Because the location of the imaging region 112 is a prior known in worldcoordinates to the locator module 132, the relative distance between the ROI 126 and the imaging region 112 can be computed for example by taking the Euclidean distance. When setting up the nudging system 120, the location of the one or more position sensors 134 and their settings may be used in a prior calibration with the world-coordinate system, so that the locator module 132 can map the image information to real world distance for the distance between the ROI 126 and imaging region 112. Similar 3D or 2D geometrical computations may also be applied when using localization modules LM which operate based on different localization principles.

The incoming location signal may be an at least partial back-reflection signal or a back-scatter signal of, in particular, the outgoing nudging signal. The ultrasound nudging signal itself may hence be used in a dual role for nudging and for ROI location. Echo location may be used to establish the distance between the ROI 126 and the imaging region 112. The control circuitry 128 may control the transmitter 122 to operate in either of two modes, a nudging mode or in location mode and to switch rapidly between the two as required. When operating in location mode, the frequency of the emitted ultrasound signal may be changed so that no nudging sensation is induced in the patient's skin. The outgoing ultrasound wave directed from the transmitter 122 is emitted and reflected back and received as an incoming signal at the position sensor 134, which in this example comprises a receiver. An evaluation of an incurred Doppler shift may then be used to establish the position of the ROI 126. The receiver 134 and the transmitter 122 may be arranged combined into a single unit as a transceiver. As explained above in terms of camera-based ROI location, the ultrasound-based ROI location can be mapped into the world co-ordinate system to establish the relative distance between the imaging region 112 and the current position of the ROI 126. In other words, the ultrasound system may be used as a closed-looped control system. Specifically, the location of the ROI 126 is monitored and, in response to the current position of the ROI 126, and hence of the relative distance to the imaging region 112, the nudging signal is adapted by changing modulation and/or direction. In particular, a direction of the nudging signal and/or (pulse) frequency and/or intensity may be suitably modulated in dependence of the measured distance. As mentioned above, once the ROI 126 is within the imaging region 112, the nudging signal may subside, but the locator module 132 may continue to monitor the position of the ROI 126. If the location module 132 registers motion of the ROI 126 within the imaging region 112, the nudging signal is re-emitted to encourage the patient to move or re-posture so that the ROI 126 remains within the imaging region 112.

Figure 2:
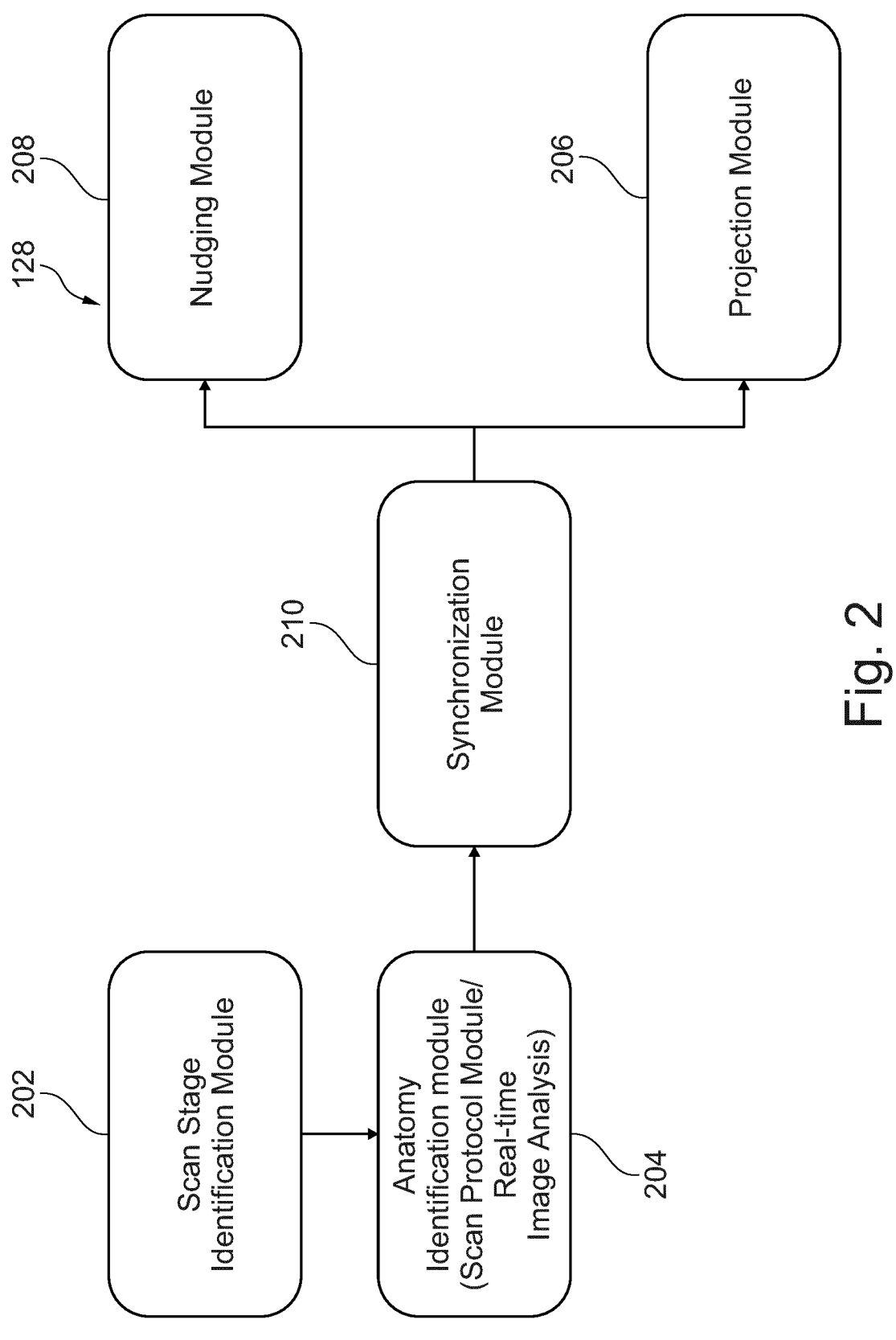
FIG. 2 shows control circuitry for the medical imaging system of FIG. 1.

FIG. 2 illustrates the control circuitry 128 of the medical imaging system 100 in more detail. The control circuitry 128 is configured to control the medical imaging system 100 to provide synchronized display and nudging to provide a patient with information on the progress of a scan. The control circuitry 128 comprises a scan stage identification module 202, an anatomy identification module 204, a projection module 206, a nudging module 208, and a synchronization module 210.

The scan stage identification module 202 is configured to identify a stage of the scan based on a predetermined scan sequence. The scan stage identification module 202 may automatically identify the stage of the scan using sequence/protocol data relating to the scan. The scan sequence for the complete examination is known from the prior planning. The stage of the scan may comprise an indication of the current and/or next scan. The status of the actual scan is communicated to the patient 104 in the bore 116 via the display system 138 and via the nudging system 120.

The anatomy identification module 204 (which may also be called a relevant anatomy identification module) is configured automatically to identify one or more relevant anatomical regions for the current and/or next scan. This may be determined from the selected type of scan (e.g. specific pre-defined scan for lower periphery), from information specified during scan planning (staff specifies field of view of scan relative to body), or from sensors (for example, the position sensor 134 or a drive of the examination table 118 may detect which anatomical region is in the isocenter of the scanner). In particular, in MR as well as CT scanning, scans are typically selected from a database of scans that is ordered per anatomy. This information may be input to the anatomy identification module 204. In MRI, staff typically prepare the scan by first executing a scout scan with a large field of view, e.g. the entirety of the lower limbs, and then specify a local field of view for a particular scan of one organ, e.g. the left lower leg. This may serve as input to the anatomy identification module 204. In MRI, dedicated coils are often applied to certain organs, e.g. a knee coil. If the scan is executed with this kind of coil, this information may serve as input to the anatomy identification module 204. In CT, the ROI 126 may be defined after execution of a scout scan and using the definition of the scan protocol and the individual scan parameters. The information about the exact start/stop position may be extracted from the low dose scout scan image and translated into patient table positions and scan acquisition positions including the x-ray dose settings. This information can be used by the anatomy identification module 204. Normally the patient does not know this information in detail. However, in autonomous imaging, this information may be provided to the patient in an understandable way to encourage cooperation and understanding of the process. This helps to minimize motion artifacts, movements away from the defined scan regions, wrong breathing patterns and other image quality influencing effects. If there no information available from any of the above sources, the position sensor 134 (which may comprise one or more of a camera, a patient silhouette detector, a 3D camera) may be used to determine which anatomical region is currently in the isocenter of the scanner.

The projection module 206 is configured to generate images for display to the patient 104 by the display system 138 of the medical imaging system 100. As mentioned above, in one example, the display system 138 comprises an optical projection system 136. The projection module 206 instructs the optical projection system 136 to display to project images onto the patient or onto the wall of the bore 116 that illustrate the actual workflow status, the next steps and scans and the overall progress of the procedure. A color-coded scan progress indicator may be projected onto the inner wall of the bore 116 in combination with the anatomy information and the scan planning. Another option is direct projection of the scan progress indicator onto the patient's body, for example onto an anatomical region of the patient's body identified as being relevant for the current or next scan. In this way, a visualization is provided to the patient also when the patient 104 is inside the scanner. This requires suitable positioning of the displayed information and/or a mirror arrangement and/or other methods to bring the overlaid information to the patient's view. Some information may be displayed already before the patient 104 is moved onto the examination table 118 and into the scanner and some information may be displayed only inside the bore 116. Part of the information projected outside the bore 116 may indicate for example the body area that will be moved into the bore 116, so that the patient 104 knows in advance the final body position for the scanning start and with the projected ROI 126 and also the end position inside the bore 116 being visible. Good pre-information may be effective in ensuring patient satisfaction and patient trust in the system 100.

Figure 3A:
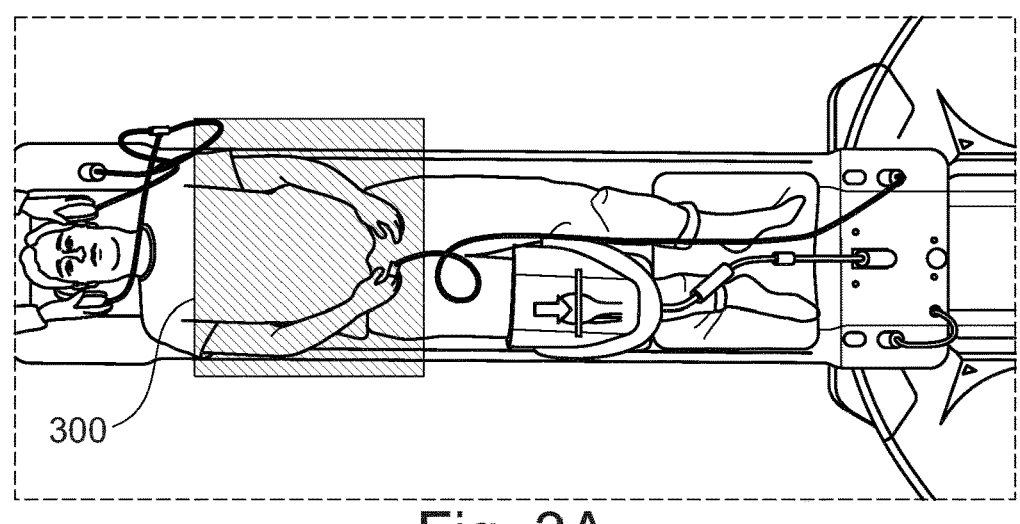
FIG. 3 shows a scan progress indicator projected onto the patient's body during imaging by the medical imaging system of FIG. 1.
Figure 3B:
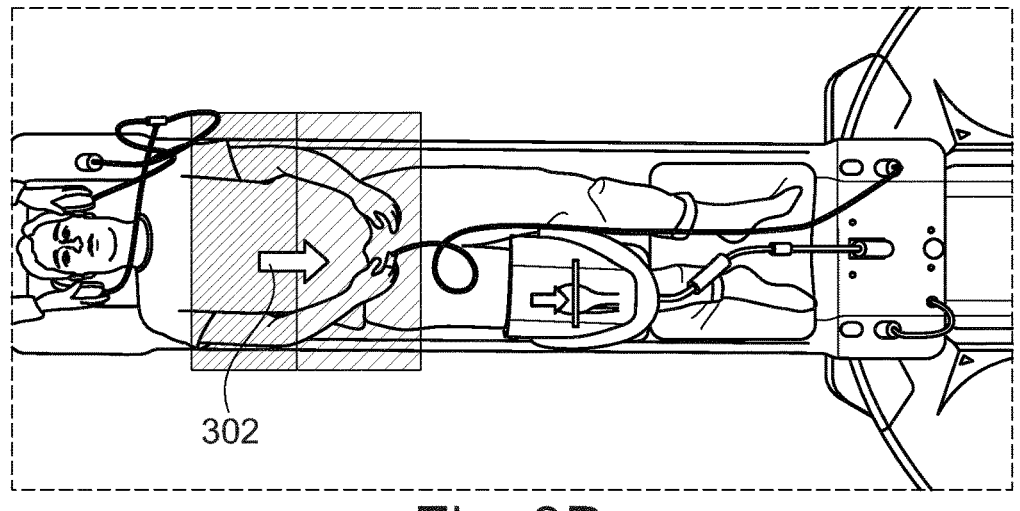
Figure 3C:
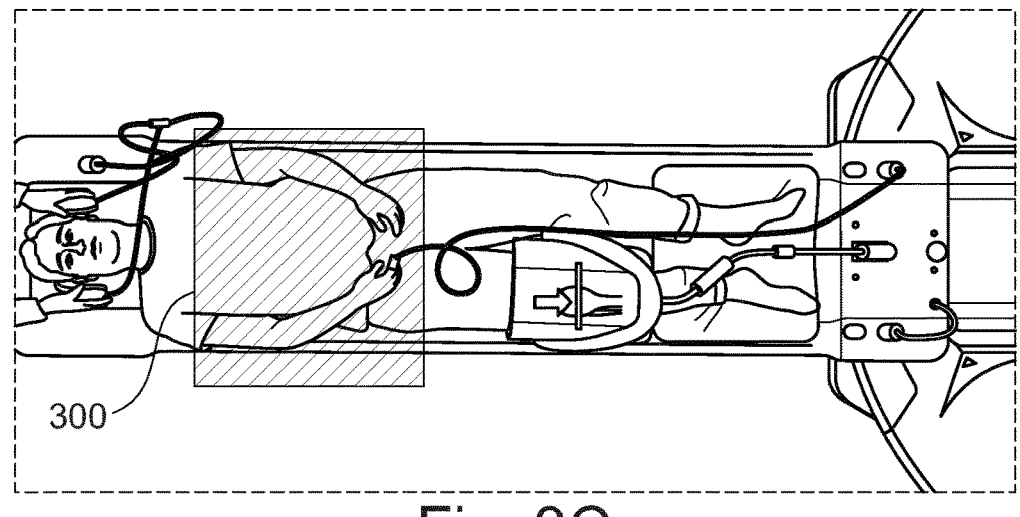

As shown in FIG. 3, the scan progress indicator 300 may take the form of a color-coded patch projected by the optical projection system 136 onto the relevant anatomical region of the patient's body. In autonomous imaging scenarios, such as for MRI/CT, it is beneficial that the patient 104 receives information about the scan, for example the region being scanned, the scan progress, and the interactions that are expected from the patient 104 during the scan at specific points of time. The color-coded patch 300 provides information about the scan region to the patient 104 prior to and during the scan, e.g. on the examination table 118 outside of the bore 116 but more importantly inside the bore 116. The projected information is synchronized with coded nudging, as described further below, to communicate with the patient and to inform about scan progress and requested activities ("breathing", "no movement", etc.) in alignment with the defined scan protocol. The projection may include different types of color coding indicating for example the start of the scan of the particular anatomical region, the current progress of the scan and the end of the scan. For example, FIG. 3A shows the patch 300 projected onto the patient's torso being colored e.g. red/orange to indicate that the scan is about to begin or is just beginning and that movement should therefore be minimized or avoided. FIG. 3B shows the midpoint of the same scan, with the patch 300 now being colored blue to indicate that part of the scan which has been completed and red/orange to indicate the remaining part of the scan to be completed, with the scan being performed from left to right in FIG. 3B, or in a top down fashion from the perspective of the patient. The patch 300 thus forms a progress bar in which the advancement of the bar is directly proportional to the amount of work that has been completed, thereby providing the user with an estimate of how far through the scan the system 100 has progressed. A scan direction indicator in the form of e.g. an arrow 302 may also be provided to indicate the direction of the scan. FIG. 3C shows the endpoint of the same scan, where the patch 300 is now colored green to indicate that the scan is complete, and that the covered anatomical region may now be moved. In a variant, the patch 300 may continuously change color (e.g. red to green) to show the progress of the scan.

For the best preparation of the patient 104, the anatomical region of the patient's body to be scanned may already be shown to the patient by means of projection and colored information when the patient is outside the bore 116. This pre-information helps to recognize the detailed stages of the scan and the progress during the scan and also for highlighting the requested patient behavior during the scan.

The nudging module 208 is configured to generate control signals for the nudging system 120 of the medical imaging system 100. The nudging module 208 uses coded signals, as described further below, to trigger the patient and inform the patient about the sequence, timing and next scans. In the case that the nudging system 120 comprises a bi-directional nudging and feedback sensor, validation and acceptance messages may be received by the system 120 from the patient and options for patient control may also be provided.

The synchronization module 208 (synchronized projection and nudging module) is configured to receive input from the scan stage identification module 202 and from the anatomy identification module 204 and to provide synchronization signals to the projection module 206 and to the nudging module 208 to synchronize the display and nudging. This will improve drawing the attention of the patient to a particular organ, which may for example be scanned next and which should remain still. In one example, a colored patch is projected onto the organ, as shown in FIG. 3, with the patch being modulated to flash (on/off) e.g. five times at a frequency of 2 Hz before the organ is scanned. Simultaneous remote nudging of that organ is performed with the exact same frequency and in phase with flashing. The projection of the scan progress indicator is thus synchronized with the interactive coded nudging. Such synchronization allows for further examples of specific communication with the patient during the scan. Actions like breathing pattern and no-movement can be indicated exactly at the point of time when the scan-protocol indicates this should be performed to achieve the best image quality. The points of time may be derived from the planned scan protocol, the real time image analysis and the system progress information according to the scan stage with the help of the anatomy identification.

The control circuitry 128 may thus be configured to control the medical imaging system to synchronize modulations in the nudging with changes made to a displayed scan progress indicator. In particular, the control circuitry 128 may be configured to control the medical imaging system 100 to modulate the nudging in synchronization with corresponding modulations made to the display, the synchronized modulations defining a coded signal to be conveyed to the patient. For example, the coded signal may indicate the start or end of the scan or that the scan will start or end after a predetermined time period elapses. Thus, the control circuitry 128 is configured to modulate onto the nudging signal further information intended for the patient. The information may be modulated by frequency and/or amplitude modulation or other to cause a modulation pattern that represents a coded signal. The nudging signal thus encodes the information in the modulation pattern. In this manner, a coded haptic signal may be created by the control circuitry 128. The coded haptic signal may be used during imaging procedures, not only for imparting instructions such as "hold breath", "stay still", but also in relation to providing other information on imaging or imaging supporting clinical procedure to be performed. Possible modulation patterns may include any one or more of the following: different count of pulses, either absolute or per unit time (frequency), different intensities (amplitude), different durations of the application of a sequence of pulses. Any one of the above-mentioned patterns may encode any one of the following: a positioning request, an amount by which a certain body part should be moved/shifted/turned etc., an indication that a procedure is underway, etc. The coded signal may be used for compliance/cooperation checking. The displayed images may represent the semantic meaning of a specific modulation pattern in terms of explanatory text and/or imagery which explains or decodes for the patient what the modulation pattern, the encoding, means.

Although the above-described medical imaging system 100 comprises a CT scanner, it will be appreciated that the invention is applicable to other medical imaging techniques such as MRI. In MRI, the detecting unit 110 comprises one or more radio frequency coils that are capable of picking up radio wave signals. The radio wave signals are emitted by disturbed protons in patient tissue when relaxing back into alignment with a strong magnetic field generated by the MRI imager during the imaging.

It will be understood that nudging may be provided using techniques other than ultrasound. For instance, the transmitter 122 may comprise one or more air nozzles configured to issue a jet of directed air to thereby cause the haptic sensation and to effect the nudging. In other examples, one or more electromagnetic radiation-based transmitters 122 are used that are configured to cause haptic sensations. Specifically, the electromagnetic radiation is configured to excite mechanoreceptors embedded in the patient's skin. The transmitter 122 may comprise a laser transmitter operable at a suitable frequency. An electromagnetic field such as laser light can also create a haptic effect at a distance from the source of excitation. Heat radiation may be used. Certain receptors (e.g., TRPV1) in human skin respond not only to heat but also to pain. By eliciting both responses in turn, a haptic sensation can be caused. This may be achieved by controlling a heat source, such as a halogen lamp or other, serving as the transmitter 122, which is suitably focused using one or more reflectors and the focus is rapidly switched. Any combination of these techniques may be used.

The subject-matter described herein may be applied to optimize or improve radiology workflow in medical imaging applications such as MRI, CT, AMI, DXR, etc. The workflow procedure and the technical implementation can be applied in particular to CT and MRI scanning. However, there are small differences especially with respect to the patient actions during the scanning. Normally the CT scan is performed over a much shorter time period. For this reason, the timing of the nudging and the type of coded signals are preferably short and precise to achieve short delay times and immediate patient reaction. For MRI, the overall scanning time is normally much longer and in this case the trade-off in the time-quality optimization may influence the timing and type of nudging commands for the patient.

Figure 4:
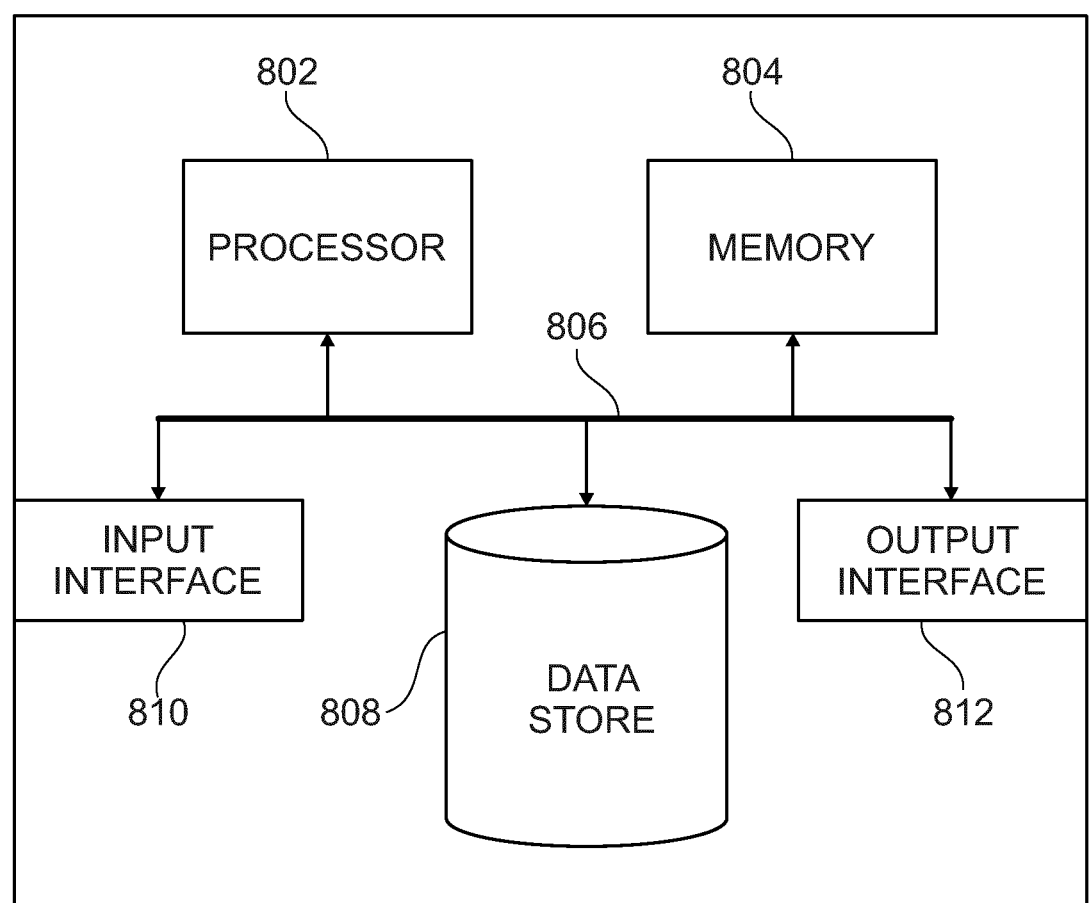
FIG. 4 illustrates a computing device that can be used in accordance with the systems and methods disclosed herein.

Referring now to FIG. 4, a high-level illustration of an exemplary computing device 800 that can be used in accordance with the systems and methodologies disclosed herein is illustrated. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store conversational inputs, scores assigned to the conversational inputs, etc.

The computing device 800 additionally includes a data store 808 that is accessible by the processor 802 by way of the system bus 806. The data store 808 may include executable instructions, log data, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

It will be appreciated that the aforementioned circuitry may have other functions in addition to the mentioned functions, and that these functions may be performed by the same circuitry.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features.

It has to be noted that embodiments of the invention are described with reference to different categories. In particular, some examples are described with reference to methods whereas others are described with reference to apparatus. However, a person skilled in the art will gather from the description that, unless otherwise notified, in addition to any combination of features belonging to one category, also any combination between features relating to different category is considered to be disclosed by this application. However, all features can be combined to provide synergetic effects that are more than the simple summation of the features.

While the invention has been illustrated and described in detail in the drawings and foregoing description, such illustration and description are to be considered exemplary and not restrictive. The invention is not limited to the disclosed embodiments.

Other variations to the disclosed embodiments can be understood and effected by those skilled in the art, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used advantageously. A computer program may be stored/distributed on a suitable medium, such as an optical storage medium or a solid-state medium supplied together with or as part of other hardware, but may also be distributed in other forms, such as via the internet or other wired or wireless communications systems. Any reference signs in the claims should not be construed as limiting the scope.

LIST OF REFERENCE SIGNS 100 medical imaging system
102 imaging apparatus
104 patient
106 x-ray beam
108 x-ray source
110 x-ray sensitive detector
112 imaging region
114 display device
116 bore
118 examination table
120 nudging system
122 nudging signal transmitter
124 impact region
126 region of interest (ROI)
128 control circuitry
130 user interface 132 locator module
134 location signal receiver
136 display screen/optical projection system
138 display system
140 digital image processor
142 medical image
202 scan stage identification module
204 anatomy identification module
206 projection module
208 nudging module
210 synchronization module
300 scan progress indicator
302 scan direction indicator
800 computing device
802 processor
804 memory
806 system bus
808 data store
810 input interface
812 output interface

The invention claimed is:

1. Control circuitry for a medical imaging system, the control circuitry comprising circuitry configured to control the medical imaging system to provide synchronized display and nudging to provide a patient with information on the progress of a scan wherein the control circuitry is further configured to control the medical imaging system to modulate the nudging in synchronization with corresponding modulations made to the display, the synchronized modulations defining a coded signal to be conveyed to the patient.

2. The control circuitry of claim 1, further configured to control the medical imaging system to project a scan progress indicator onto the patient's body.

3. The control circuitry of claim 2, further configured to control the medical imaging system to project the scan progress indicator onto an anatomical region of the patient's body identified as being relevant for the current or next scan.

4. The control circuitry of claim 1, further configured to control the medical imaging system to synchronize modulations in the nudging with changes made to a displayed scan progress indicator.

5. The control circuitry of claim 1, wherein the synchronized modulations defining the coded signal to be conveyed to the patient comprise one or more of the following modulation patterns: different absolute count of pulses; different frequency of pulses; different intensities; different durations of the application of a sequence of pulses.

6. The control circuitry of claim 5, wherein the coded signal indicates the start or end of the scan or that the scan will start or end after a predetermined time period elapses.

7. The control circuitry of claim 5, wherein the synchronized modulations have the same frequency and phase.

8. The control circuitry of claim 1, further configured to control the medical imaging system to provide intermittent nudging to an anatomical region of the patient's body in synchronization with flashing of a scan progress indicator projected onto the said anatomical region, to indicate that the said anatomical region is the next to be scanned.

9. The control circuitry of claim 1, further comprising
a scan stage identification module configured to identify a stage of the scan based on a predetermined scan sequence;
a relevant anatomy identification module configured to identify one or more relevant anatomical regions for the scan;

a projection module configured to generate images for display to the patient by a display system of the medical imaging system;

a nudging module configured to generate control signals for a nudging system of the medical imaging system; and a synchronization module configured to receive input from the scan stage identification module and from the relevant anatomy identification module and to provide synchronization signals to the projection module and to the nudging module to synchronize the display and nudging.

10. A medical imaging system comprising the control circuitry of claim 1.

11. The medical imaging system of claim 10, further comprising a display system configured to display images to the patient and a nudging system configured to provide nudging to the patient.

12. The medical imaging system of claim 10, wherein the nudging system comprises a bi-directional nudging and feedback system, and wherein the patient is provided with the information on the progress of the scan as part of a guided human-machine interaction process.

13. A method for controlling a medical imaging system, the method comprising controlling the medical imaging system to provide synchronized display and nudging to provide a patient with information on the progress of a scan.

14. A computer program product comprising computer executable instructions stored on a non-transitory computer readable medium which, when executed by a computer, enable the computer to perform the method of claim 13.

15. A non-transitory computer readable medium having stored thereon computer executable instructions which, when executed by a computer, enable the computer to perform the method of claim 13.

\* \* \* \* \*